United States Patent
Åhl et al.

(10) Patent No.: US 10,369,266 B2
(45) Date of Patent: Aug. 6, 2019

(54) MULTIPART FLUID SYSTEM AND A SYSTEM FOR CITRATE ANTICOAGULATION IN AN EXTRACORPOREAL BLOOD CIRCUIT

(71) Applicant: Gambro Lundia AB, Lund (SE)

(72) Inventors: Petra Åhl, Gällivare (SE); Gabriela Godaly, Lund (SE); Jan Sternby, Lund (SE); Anders Wieslander, Lund (SE)

(73) Assignee: GAMBRO LUNDIA AB, Lund (SE)

( * ) Notice: Subject to any disclaimer, the term of this patent is extended or adjusted under 35 U.S.C. 154(b) by 355 days.

(21) Appl. No.: 14/779,836

(22) PCT Filed: Apr. 30, 2014

(86) PCT No.: PCT/EP2014/058853
§ 371 (c)(1),
(2) Date: Sep. 24, 2015

(87) PCT Pub. No.: WO2014/177630
PCT Pub. Date: Nov. 6, 2014

(65) Prior Publication Data
US 2016/0106778 A1    Apr. 21, 2016

(30) Foreign Application Priority Data
Apr. 30, 2013 (SE) ..................... 1350534

(51) Int. Cl.
*A61M 1/36* (2006.01)
*A61K 33/00* (2006.01)
(Continued)

(52) U.S. Cl.
CPC ......... *A61M 1/3672* (2013.01); *A61K 9/0019* (2013.01); *A61K 9/0026* (2013.01);
(Continued)

(58) Field of Classification Search
CPC .............. A61K 2300/00; A61K 31/194; A61K 31/7004; A61K 33/10; A61K 33/14;
(Continued)

(56) References Cited

U.S. PATENT DOCUMENTS

2007/0062861 A1    3/2007    Lannoy
2007/0110829 A1    5/2007    Tolwani et al.
(Continued)

FOREIGN PATENT DOCUMENTS

WO    2007101064    9/2007
WO    2010112538    10/2010
WO    2011109356    9/2011

*Primary Examiner* — John Kim
(74) *Attorney, Agent, or Firm* — K&L Gates LLP

(57) ABSTRACT

The present invention concerns a multipart fluid system for dialysis therapy, wherein the multipart fluid system comprises an anticoagulation fluid and at least one treatment fluid from the group consisting of dialysis fluid and infusion fluids. According to the invention the anticoagulation fluid comprises 15-40 mM citrate; and the at least one treatment fluid comprises 1.5-8 mM citrate and ≥10 mM bicarbonate. The present invention further concerns a system for citrate anticoagulation in an extracorporeal blood circuit.

12 Claims, 5 Drawing Sheets

(51) Int. Cl.
*A61K 33/10* (2006.01)
*A61K 33/42* (2006.01)
*A61K 31/225* (2006.01)
*A61K 31/7004* (2006.01)
*A61M 1/34* (2006.01)
*A61M 1/16* (2006.01)
*A61K 31/194* (2006.01)
*A61K 33/14* (2006.01)
*A61K 9/00* (2006.01)
*A61K 33/06* (2006.01)
*A61K 47/02* (2006.01)

(52) U.S. Cl.
CPC .......... *A61K 31/194* (2013.01); *A61K 31/225* (2013.01); *A61K 31/7004* (2013.01); *A61K 33/00* (2013.01); *A61K 33/06* (2013.01); *A61K 33/10* (2013.01); *A61K 33/14* (2013.01); *A61K 33/42* (2013.01); *A61M 1/1654* (2013.01); *A61M 1/1672* (2014.02); *A61M 1/342* (2013.01); *A61M 1/3434* (2014.02); *A61M 1/3437* (2014.02); *A61M 1/3441* (2013.01); *A61K 47/02* (2013.01); *A61M 1/3675* (2013.01)

(58) Field of Classification Search
CPC ...... A61K 33/42; A61K 33/225; A61K 33/00; A61K 33/06; A61K 47/02; A61K 9/0019; A61K 9/0026; A61M 1/1654; A61M 1/1672; A61M 1/342; A61M 1/3434; A61M 1/3437; A61M 1/3441; A61M 1/3672; A61M 1/3675
See application file for complete search history.

(56) References Cited

U.S. PATENT DOCUMENTS

2008/0015487 A1  1/2008  Szamosfalvi et al.
2012/0022423 A1*  1/2012  Sternby ................ A61K 31/191
                                                     604/6.07

\* cited by examiner

MULTIPART FLUID SYSTEM AND A SYSTEM FOR CITRATE ANTICOAGULATION IN AN EXTRACORPOREAL BLOOD CIRCUIT

PRIORITY CLAIM

This applicaion is a 371 National Stage Application of International Application No. PCT/EP2014/058853, filed Apr. 30, 2014, which claims priority to and the benefit of Swedish Application No. 1350534-2, filed Apr. 30, 2013, the disclosures of each of which are incorporated by reference herein in their entireties.

TECHNICAL FIELD

The present invention concerns a multipart fluid system for dialysis therapy. More particularly it relates to an anticoagulation fluid and at least one treatment fluid from the group consisting of a dialysis fluid and an infusion fluid.

The present invention further concerns a system for citrate anticoagulation in an extracorporeal blood treatment.

BACKGROUND

Dialysis is the indicated treatment for patients with renal insufficiency. The removal of waste substances and excess of fluid from the blood is effected by transfer to an external fluid or by replacement of plasma liquid with an external fluid. Various dialysis techniques with associated dialysis fluids may be differentiated. Which dialysis technique to use, depends on the type of patient.

In the case of patients suffering from chronic renal insufficiency, the patient receives dialysis therapy 3-5 hours, about three times per week. The dialysis therapy is usually performed at a dialysis center, although home dialysis is also possible. When home dialysis is performed the patient is free to perform dialysis more frequently and also in a more gentle treatment with longer duration, i.e. 4-8 hours per treatment and 5-7 treatments per week. The dose and treatment duration may be adjusted to each patient's demands and needs.

In the case of patients suffering from acute renal insufficiency, a continuous treatment throughout the entire day, and in some cases for several weeks, a continuous renal replacement therapy (CRRT), is the indicated treatment.

Continuous renal replacement therapy (CRRT) is also the treatment mode when a patient with chronic renal insufficiency is using a wearable artificial kidney system. Such a system is for example disclosed in US2008/058696.

In a dialysis therapy a portion of the patient's blood stream is lead into an extracorporeal blood circuit comprising a semipermeable membrane in which the removal of waste substances and excess fluid is performed and then the cleansed blood is lead back to the patient. The semipermeable membrane has a blood side and a dialysate side.

When the removal of waste substances is effected by transfer to an external fluid, the waste substances and excess fluid are transferred by diffusion through the semipermeable membrane wall into a dialysis fluid flowing on the dialysate side of the semipermeable membrane. Simultaneously as the waste substances are transferred from the blood, through the semipermeable membrane wall and into the dialysis fluid, solutes and nutrients may diffuse in the opposite direction from the dialysis fluid, through the semipermeable membrane and into the blood. This technique is called hemodialysis.

When the removal of waste substances is made by replacement of plasma liquid with an external fluid, a portion of the plasma liquid is removed from the blood by means of convective flow through the semipermeable membrane, and an external fluid (also called an infusion fluid, a replacement fluid or a substitution fluid) is added to the blood stream. This technique is called hemofiltration.

Finally the removal of waste substances may also be made by a combination of hemodialysis and hemofiltration. Thus the removal of waste substances is provided by a combination of diffusion and convection through the semipermeable membrane, and the solutes and nutrients are added both by infusion in the blood stream and by diffusion from the dialysis fluid through the semipermeable membrane and into the blood. This technique is called hemodiafiltration.

Common for all the above disclosed techniques is that the blood is withdrawn from the patient continuously into an extracorporeal blood circuit, in which the removal takes place, and the "cleansed" blood is returned to the patient. When blood is removed from its normal environment within the blood vessels, the blood coagulation cascade is initiated, and in order not to clog the extracorporeal blood circuit with the coagulating blood, means for anticoagulation have to be provided.

The fluids used during the dialysis therapy thus the dialysis fluid, the infusion fluid (also named replacement fluid or substitution fluid), have been given the comprehensive term "treatment fluids" in the following.

The treatment fluids used in all the above dialysis techniques contain mainly electrolytes like sodium, magnesium, calcium, potassium, an acid/base buffer system and optionally glucose or a glucose-like compound. All the components in the treatment fluids are selected to control the levels of electrolytes and the acid-base equilibrium within the blood.

The treatment fluids are today often prepared from different types of concentrates. It may be liquid concentrates of different degree of concentration, where the acid/electrolyte part is usually separated from the buffer part before use.

The treatment fluids may be prepared from concentrated volumes of 0.5-8 L in bags for bedside use, or prepared from volumes of 5-20 L in canisters, which still are for bedside use. The treatment fluids may also be prepared from concentrates in central tanks in volumes of 300-1000 L.

The concentrates may also be provided as dry powder concentrate, to be dissolved and diluted into the determined concentrations.

When using bicarbonate as a buffer component in the treatment fluids, bicarbonate may also be provided as a dry concentrate for on-line-preparation of saturated bicarbonate containing concentrate. The saturated bicarbonate containing concentrate is thereafter mixed with an acid/electrolyte concentrate and further diluted with purified water to produce the on-line prepared treatment fluid.

The treatment fluids may also be provided in bags. In some cases the treatment fluids are provided in multiple compartment bags, in which the acid/electrolyte part is contained within one compartment, and the buffer part is contained in another compartment, and where the two parts are mixed right before use in a way to maintain sterility of the treatment fluid to provide a ready-for-use treatment fluid. Also, the treatment fluid may be provided in single compartment bags.

Citrate anticoagulation has in recent years proven to be an equivalent candidate to heparin for critically ill patients treated with continuous renal replacement therapy (CRRT), and has also been suggested for use as anticoagulant in chronic dialysis therapy. Metabolic complications are less severe with citrate, but may lead to a more labor intensive monitoring of arterial blood gases and calcium.

When citrate anticoagulation is used in dialysis therapies, the concentration of citrate is often quite high in order to limit the amount of anticoagulation fluid infused to the extracorporeal circuit. The infusion of anticoagulation fluid also adds considerable amounts of sodium to the patient, which has been compensated by lower sodium levels in the other treatment fluids. This problem has also been addressed by the anticoagulation fluid Prism0citrate™ of Gambro, which fluid contains 12 mM citrate and a physiological level of sodium. However, this low citrate concentration requires a high infusion rate of the anticoagulation fluid, which leads to situations when too much of the desired treatment dose is supplied by the anticoagulation fluid, leaving too little room for using other treatment fluids. A modified citrate containing anticoagulation fluid has therefore been developed containing 18 mM citrate.

The standard treatments with citrate anticoagulation also required an infusion of calcium fluid. This may be avoided by applying the concept disclosed in (WO2010/112538), where in one embodiment both calcium and citrate are present in all the fluids. The required levels of citrate are then higher, since some of the citrate will be complex bound to the added calcium. The citrate reaching the patient will be metabolized whereby bicarbonate is produced. This must be taken into account when the bicarbonate levels of the treatment fluids are determined.

However, a high concentration of citrate in the anticoagulation fluid demands a reduction of the bicarbonate level in the other treatment fluids. The reduction needed will however depend on the flow rates of these fluids. If imbalance created by the anticoagulation fluid is large, the possible interval of flow rates for the treatment fluids will be very small, and this will limit the treatment options in terms of dose.

Today a number of citrate anticoagulation protocols offer high solute clearance, but none of the proposed systems provide proper acid-base control using one standard citrate anticoagulation fluid, and at least one of a standard infusion fluids and a standard dialysis fluids.

SUMMARY OF THE INVENTION

One object of the present invention is to provide a multipart fluid system for citrate anticoagulation in which the concentrations of citrate and bicarbonate are balanced between the fluids to provide an acid-base balance within the patient throughout the treatment.

Another object of the present invention is to provide a multipart fluids system for citrate anticoagulation which provides the possibility to vary the flow rates of the different fluids within the multipart fluid system in large intervals without causing any acid-base imbalance within the patient.

The present invention concerns a multipart fluid system for acute and chronic dialysis therapy, wherein the multipart fluid system comprises an anticoagulation fluid and at least one treatment fluid from the group consisting of dialysis fluid and infusion fluids. According to the invention the anticoagulation fluid comprises 15-40 mM citrate, and the at least one treatment fluid comprises 1.5-8 mM citrate and ≥10 mM bicarbonate.

The present invention further concerns a (first) system for citrate anticoagulation in an extracorporeal blood circuit comprising an arterial blood line configured to be connected to a vascular access for withdrawing blood from a patient and a venous blood line configured to be connected to the vascular access for returning blood to the patient. According to the invention, the system comprises a filter with a dialysate side and a blood side; which blood side is in fluid communication with the arterial and venous blood lines; and which blood side is in fluid communication with an anticoagulation fluid source comprising 15-40 mM citrate; a treatment fluid source comprising 1.5-8 mM citrate and ≥10 mM bicarbonate with fluid communication with at least one of the blood side or dialysate side of the filter.

In one embodiment of the present invention said anticoagulation fluid (or anticoagulation fluid source) comprises 15-40 mM citrate, preferably 18-40 mM citrate, more preferably 20-30 mM citrate.

In another embodiment of the present invention said at least one treatment fluid (or source of treatment fluid) comprises ≥0 mM, preferably 10-30 mM, more preferably 10-25 mM, most preferably 10-20 mM bicarbonate.

In another embodiment of the present invention said at least one treatment fluid (or source of treatment fluid) comprises 1-5 mM total calcium.

In yet another embodiment of the present invention said at least one treatment fluid (or source of treatment fluid) comprises 2.0-7.0 mM citrate and 1.8-2.4 mM total calcium.

In even another embodiment of the present invention said at least one treatment fluid (or source of treatment fluid) comprises 3.5-5.5 mM citrate and 1.8-2.4 mM total calcium.

In another embodiment said at least one treatment fluid (or source of treatment fluid) further comprises 0-1.5 mM magnesium, 0-5.0 mM potassium, 0-11 mM glucose, 130-150 mM sodium.

In one embodiment said at least one treatment fluid (or source of treatment fluid) may further comprises 0.1-2.0 mM phosphate, preferably 0.4-1.5 mM phosphate, more preferably 0.6-1.2 mM phosphate.

In one embodiment said anticoagulation fluid (or anticoagulation fluid source) may further comprise 1.5-4 mM total calcium, preferably 1.5-3 mM total calcium, more preferably 1.5-2.4 mM total calcium.

In yet another embodiment said anticoagulation fluid (or anticoagulation fluid source) may further comprise 0-1.5 mM magnesium, 0-5.0 mM potassium, 0-11 mM glucose, 130-150 mM sodium.

In even another embodiment said anticoagulation fluid (or anticoagulation fluid source) may further comprise 0.1-2.0 mM phosphate, preferably 0.4-1.5 mM phosphate, and most preferably 0.6-1.2 mM phosphate.

With the multipart fluid system according to the present invention and the systems for citrate anticoagulation in an extracorporeal blood circuit according to the present invention a dialysis therapy which provides an acid-base balance within the patient throughout the treatment is enabled. It is also possible to vary the flow rates of the different fluids within the multipart fluid system in large intervals without causing any acid-base imbalance within the patient.

DEFINITIONS

Figure 1:
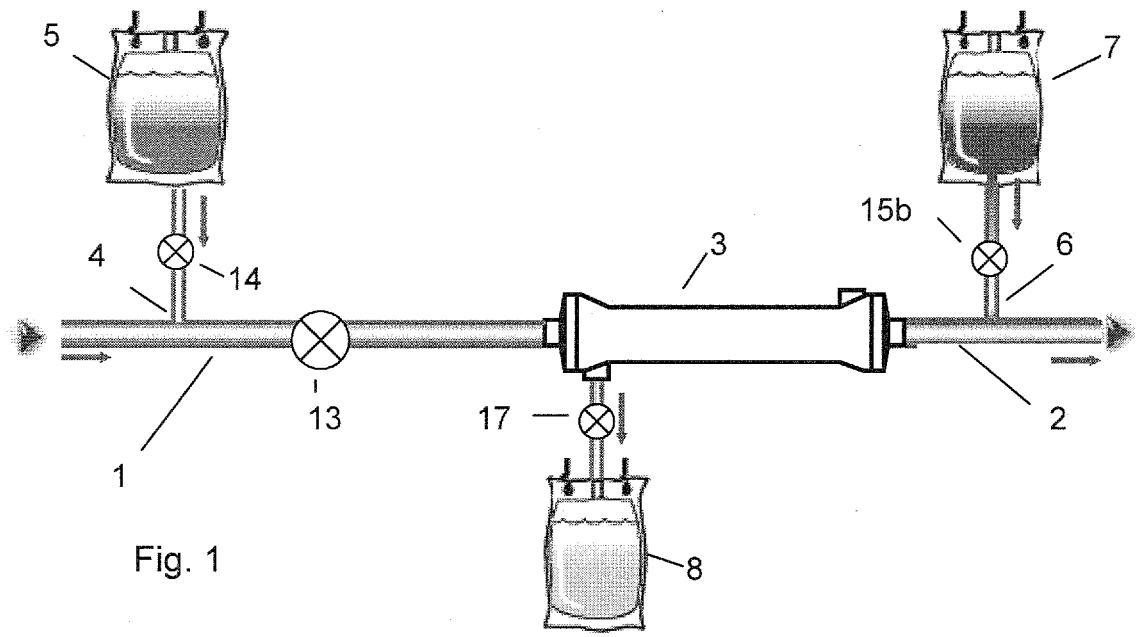
FIG. 1-8 show different embodiments of the system for citrate anticoagulation in an extracorporeal blood circuit.

The term "dialysis therapy" means all types of dialysis therapies both for chronic renal insufficiency and acute renal insufficiency.

The term "CRRT" means a continuous renal replacement therapy and this type of treatment mode is used in case of acute renal insufficiency or in case of chronic renal insufficiency when using a wearable artificial kidney system.

By the term "filter" it is herein meant a unit comprising semipermeable membranes. This unit may also be called a semipermeable membrane, a dialyzer, a dialysis filter or a dialysis membrane.

The term "anticoagulation fluid" means a fluid which is intended to provide for the anticoagulation effect within the extracorporeal blood circuit and which is intended to be infused within the extracorporeal blood circuit.

The term "anticoagulation fluid source" means the source of anticoagulation fluid. The source may be provided as fluid concentrate or in form of dry powder concentrate.

The term "treatment fluid" means a dialysis fluid for perfusion of a filter or an infusion fluid, i.e. a fluid for pre- or postinfusion. Thus, treatment fluids includes dialysis fluid, infusion fluid, replacement fluid and substitution fluid.

The term "source of treatment fluid" means the source of treatment fluid, which may be provided as fluid concentrate or in form of dry powder concentrate.

The term "dialysis fluid" means a fluid for perfusion of a filter, on the dialysate side of such a filter, opposite the blood side.

The term "infusion fluid" means a fluid which is infused into the extracorporeal blood circuit either for predilution (pre-infusion), i.e. infused into the extracorporeal blood flow before the blood enters the filter, or for postdilution (post-infusion), i.e. infused into the extracorporeal blood flow after the blood has exited the filter and before the blood is returned to the patient. Infusion fluids are normally also named as replacement fluids, substitution fluids or hemofiltration fluids.

The term "total calcium concentration" means the total concentration of calcium present in a fluid, thus representing the sum of calcium present as ionized, complex bound and protein bound calcium.

The term "citrate" means citric acid or any salt thereof. The salt may be formed with sodium, magnesium or potassium. The sodium citrate may be present as trisodium citrate, disodium hydrogencitrate, or monosodium di hydrogencitrate. The citrate may be added to the anticoagulation fluid and/or the at least one treatment fluid.

The term "phosphate" means phosphoric acid or any salt thereof. The salt may be formed with sodium, magnesium, or potassium. The component may be added as phosphate ($PO_4^{3-}$), hydrogenphosphate ($HPO_4^{2-}$) or dihydrogen phosphate ($H_2PO_4^{-}$). Examples of salts are trisodium phosphate, disodium hydrogenphosphate, monosodium dihydrogenphosphate. The phosphate may be added to the anticougulation fluid and/or the at least one treatment fluid.

DETAILED DESCRIPTION OF THE INVENTION

When using citrate for anticoagulation during a dialysis therapy, proper considerations have to be made concerning the acid/base content in the different treatment fluids to be used together with the citrate anticoagulation fluid. The concentrations of citrate and bicarbonate need to be balanced between the fluids to provide a proper acid-base balance within the patient throughout the treatment. This balance of citrate and bicarbonate is also important concerning providing the possibility to vary the flow rates of the different fluids within the fluid system (anticoagulation fluid and treatment fluids) without causing any acid-base imbalance within the patient.

In the multipart fluid system and the system for citrate anticoagulation according to the invention, the following combinations may be provided, wherein the term "anticoagulation fluid" apart from the anticoagulation fluid within the multipart fluid system, also includes the anticoagulation fluid source within the system for citrate anticoagulation, the term "treatment fluid" apart from the treatment fluid within the multipart fluid system also includes the treatment fluid source within the system for citrate anticoagulation, the term "infusion fluid" apart from the infusion fluid within the multipart fluid system also includes the infusion fluid source within the system for citrate anticoagulation, the term "dialysis fluid" apart from the dialysis fluid in the multipart fluid system also includes the dialysis fluid source within the system for citrate anticoagulation.

In one embodiment the anticoagulation fluid comprises 15-40 mM citrate, in another embodiment the anticoagulation fluid comprises 18-40 mM citrate, and in yet another it comprises 20-30 mM citrate. In another embodiment the anticoagulation fluid further comprises 1.5-4 mM total calcium, preferably 1.5-3 mM total calcium, more preferably 1.5-2.4 mM total calcium.

In yet another embodiment the anticoagulation fluid further comprises 0-1.5 mM magnesium, 0-5.0 mM potassium, 0-11 mM glucose, 130-150 mM sodium.

The anticoagulation fluid may also comprise chloride ions, for example in an amount of 0-140 mM.

In even another embodiment the anticoagulation fluid further comprises 0.1-2.0 mM phosphate, preferably 0.4-1.5 mM phosphate, and most preferably 0.6-1.2 mM phosphate.

An embodiment of the invention is an anticoagulation fluid (or anticoagulation fluid source) comprising 15-40 mM citrate, 0-4 mM calcium, 0-1.5 mM magnesium, 0-5.0 mM potassium, 0-11 mM glucose, 130-150 mM sodium; and optionally, 0.1-2.0 mM phosphate.

Said anticoagulation fluid may, according to one embodiment of the present invention, be used together with at least one treatment fluid comprising 1.5-8 mM citrate and ≥10 mM bicarbonate.

In another embodiment said at least one treatment fluid comprises 1.5-8 mM citrate and 10-30 mM bicarbonate, preferably 1.5-8 mM citrate and 10-25 mM bicarbonate.

Said at least one treatment fluid may in another embodiment further comprise 1-5 mM total calcium.

In yet another embodiment said at least one treatment fluid may comprise 2.0-7.0 mM citrate and 1.5-2.4 mM total calcium.

In another embodiment said at least one treatment fluid may comprise 3.5-5.5 mM citrate and 1.5-2.4 mM total calcium.

In further embodiments said at least one treatment fluid may further comprise 0-1.5 mM magnesium, 0-5.0 mM potassium, 0-11 mM glucose, 130-150 mM sodium.

The treatment fluid may also comprise chloride ions, preferably in an amount of 80-150 mM.

In even further embodiment said at least one treatment fluid may further comprise 0.1-2.0 mM phosphate, preferably 0.4-1.5 mM phosphate, and more preferably 0.6-1.2 mM phosphate.

An embodiment of the present invention is a treatment fluid comprising 1.5-8 mM citrate, ≥10 mM bicarbonate, for example 10-30 mM bicarbonate; 0-5 mM total calcium;

0-1.5 mM magnesium; 0-5.0 mM potassium, 0-11 mM glucose, 130-150 mM sodium, and optionally 0.1-2.0 mM phosphate.

Said at least one treatment fluid may in one embodiment be one dialysis fluid. In another embodiment the at least one treatment fluid may be one infusion fluid. In yet another embodiment the at least one treatment fluid may be one dialysis fluid and one infusion fluid. In even another embodiment said at least one treatment fluid may be two infusion fluids. In another embodiment said at least one treatment fluid may be one dialysis fluid and two infusion fluids.

Also, an invention is illustrated by the system described above as a system (first) for citrate anticoagulation in an extracorporeal blood circuit comprising an arterial blood line configured to be connected to a vascular access for withdrawing blood from a patient and a venous blood line configured to be connected to the vascular access for returning blood to the patient. According to the invention, the system comprises a filter with a dialysate side and a blood side; which blood side is in fluid communication with the arterial and venous blood lines; and which blood side is in fluid communication with an anticoagulation fluid source comprising 10-40 mM citrate, such as 15-40 mM citrate; a treatment fluid source comprising 1.5-8 mM citrate and ≥10 mM bicarbonate with fluid communication with at least one of the blood side or dialysate side of the filter.

The system as described comprises the multipart fluid system as herein described. The system comprises an anticoagulation fluid comprising 15-40 mM citrate, 0-4 mM calcium, 0-1.5 mM magnesium, 0-5.0 mM potassium, 0-11 mM glucose, 130-150 mM sodium; and optionally, 0.1-2.0 mM phosphate; in combination with a treatment fluid comprising 1.5-8 mM citrate, ≥10 mM bicarbonate, for example 10-30 mM bicarbonate; 0-5 mM total calcium; 0-1.5 mM magnesium; 0-5.0 mM potassium, 0-11 mM glucose, 130-150 mM sodium, and optionally 0.1-2.0 mM phosphate.

In another embodiment (second) the system further comprises a post-filter infusion line connected to the venous blood line downstream the filter and connected to the treatment fluid source comprising, 1.5-8 mM citrate and ≥10 mM bicarbonate to be infused into the blood stream in the venous blood line.

The system may in this second embodiment comprise a filter with a dialysate side and a blood side, which blood side is in fluid communication with the arterial and venous blood lines; a pre-filter infusion line connected to the arterial blood line upstream the filter and connected to an anticoagulation fluid source comprising 10-40 mM citrate, more particularly 15-40 mM, to be infused into the blood stream in the arterial blood line; and a post-filter infusion line connected to the venous blood line downstream the filter and connected to an infusion fluid source comprising, 1.5-8 mM citrate and ≥10 mM bicarbonate to be infused into the blood stream in the venous blood line.

In a further embodiment (third) of the system for citrate anticoagulation in an extracorporeal blood circuit the treatment fluid source is a dialysis fluid source which is in fluid communication with the dialysate side of the filter.

The system, as described as the third system above, may comprise a filter with a dialysate side and a blood side, which blood side is in fluid communication with the arterial and venous blood lines, and which dialysate side is in fluid communication with a dialysis fluid source comprising 1.5-8 mM citrate and ≥10 mM bicarbonate; and a pre-filter infusion line connected to the arterial blood line upstream the filter and connected to an anticoagulation fluid source comprising 10-40 mM citrate, such as 15-40 mM citrate, to be infused into the blood stream in the arterial blood line.

Another embodiment (fourth) of the system it further comprises a second pre-filter infusion line connected to the arterial blood line upstream the filter and connected to an infusion fluid source comprising 1.5-8 mM citrate and ≥10 mM bicarbonate to be infused into the blood stream in the arterial blood line. This system for citrate anticoagulation according to the invention may in another embodiment (fifth) further comprise a post-filter infusion line connected to the venous blood line downstream the filter and connected to an infusion fluid source comprising 1.5-8 mM citrate and ≥10 mM bicarbonate to be infused into the blood stream in the venous blood line.

The embodiment (fourth) may comprise a filter with a dialysate side and a blood side, which blood side is in fluid communication with the arterial and venous blood lines; a first pre-filter infusion line connected to the arterial blood line upstream the filter and connected to an anticoagulation fluid source comprising 10-40 mM citrate, more particularly 15-40 mM citrate, to be infused into the blood stream in the arterial blood line; and a second pre-filter infusion line connected to the arterial blood line upstream the filter and connected to an infusion fluid source comprising 1.5-8 mM citrate and ≥10 mM bicarbonate to be infused into the blood stream in the arterial blood line. Also this system for citrate anticoagulation according to the invention may in another embodiment (fifth) further comprise a post-filter infusion line connected to the venous blood line downstream the filter and connected to an infusion fluid source comprising 1.5-8 mM citrate and ≥10 mM bicarbonate to be infused into the blood stream in the venous blood line.

In other embodiments of said second, fourth and fifth system for citrate anticoagulation according to the present invention the dialysate side of the filter are in fluid communication with a dialysis fluid source comprising 1.5-8 mM citrate and ≥10 mM bicarbonate.

In even further embodiment of said system for citrate anticoagulation according to the present invention each said system may further comprise a control unit adapted to control the anticoagulation fluid flow rate in relation to the blood flow rate.

An embodiment of the invention is a multipart fluid system for dialysis therapy, comprising an anticoagulation fluid containing 30 mM citrate; and at least one treatment fluid comprising 4 mM citrate and 18 mM bicarbonate.

An embodiment of the invention is a multipart fluid system for dialysis therapy, comprising an anticoagulation fluid containing 30 mM citrate; and at least one treatment fluid comprising 5 mM citrate and 15 mM bicarbonate.

An embodiment of the invention is a multipart fluid system for dialysis therapy, comprising an anticoagulation fluid containing 18 mM citrate; and at least one treatment fluid comprising 4 mM citrate and 20 mM bicarbonate.

An embodiment of the invention is a multipart fluid system for dialysis therapy, comprising an anticoagulation fluid containing 25 mM citrate; and at least one treatment fluid comprising 5 mM citrate and 17 mM bicarbonate.

An embodiment of the invention is a multipart fluid system for dialysis therapy, comprising an anticoagulation fluid containing 30 mM citrate; and at least one treatment fluid comprising 4 mM citrate and 16 mM bicarbonate.

An embodiment of the invention is a multipart fluid system for dialysis therapy, comprising an anticoagulation fluid containing 40 mM citrate; and at least one treatment fluid comprising 5 mM citrate and 12 mM bicarbonate.

An embodiment of the invention is a multipart fluid system for dialysis therapy, comprising an anticoagulation fluid containing 15 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 16 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 17 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 18 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 19 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 20 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 22 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 25 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 30 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 35 mM citrate; and at least one treatment fluid comprising 1.5-8 mM citrate and 10-30 mM bicarbonate.

An embodiment of the invention is a multipart fluid system for dialysis therapy, comprising an anticoagulation fluid containing 40 mM citrate; and at least one treatment fluid comprising 1.5-8 mM citrate and 10-30 mM bicarbonate.

Figure 9:
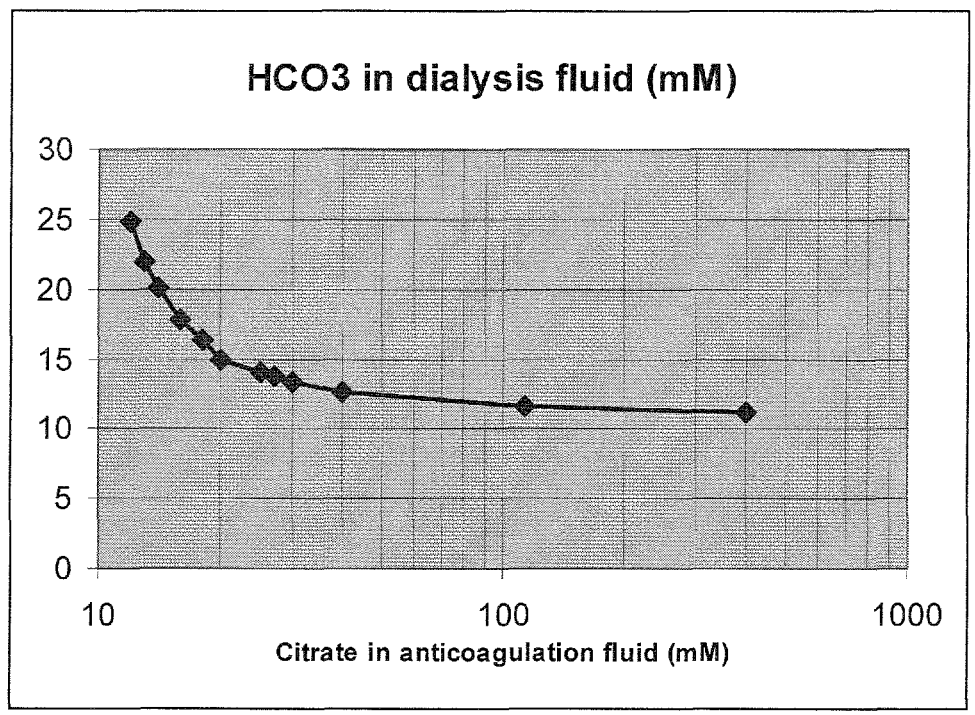
FIG. 9 shows the level of bicarbonate required when changing the concentration of citrate.

Preferably, when citrate in the anticoagulation fluid is present in the lower concentration range, i.e. from about 15 mM to about 20 mM citrate, the concentration of bicarbonate is adjusted to a lower range. This is shown in FIG. 9.

DETAILED DESCRIPTION OF THE DRAWINGS

In FIG. 1 is shown a first system for citrate anticoagulation in an extracorporeal blood circuit comprising an arterial blood line 1 configured to be connected to a vascular access (not shown) for withdrawing blood from a patient and a venous blood line 2 configured to be connected to the vascular access (not shown) for returning blood to the patient. This system comprises a filter 3 with a dialysate side and a blood side, which blood side is in fluid communication with the arterial blood line 1 and venous blood line 2; a pre-filter infusion line 4 connected to the arterial blood line 1 upstream the filter 3 for infusing an anticoagulation fluid 5 comprising 15-40 mM citrate into blood in the arterial blood line 1; and a post-filter infusion line 6 connected to the venous blood line 2 downstream the filter 3 for infusing an infusion fluid 7 comprising 1.5-8 mM citrate and ≥10 mM bicarbonate into blood in the venous blood line 2. An effluent bag 8 is provided in fluid communication with the dialysate side of the filter 3, to collect the plasma water (ultrafiltrate) withdrawn from the blood passing the filter 3.

Figure 2:
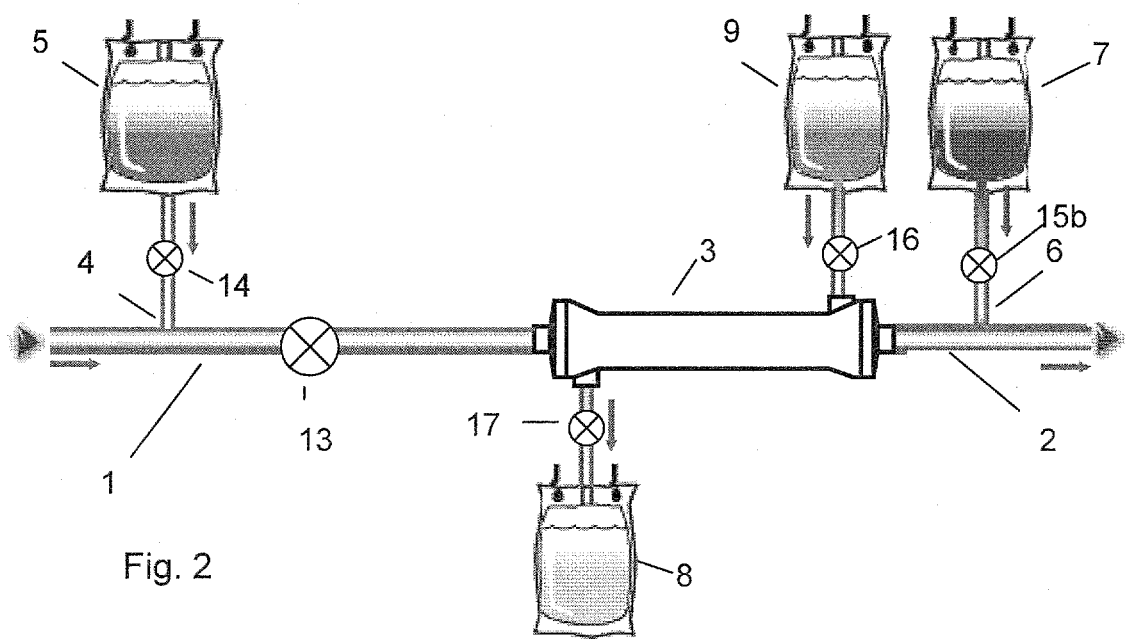

In FIG. 2 is shown another embodiment of the system in FIG. 1 with the addition that the dialysate side of the filter 3 is in fluid communication with a dialysis fluid source 9 comprising 1.5-8 mM citrate and ≥10 mM bicarbonate.

Figure 3:
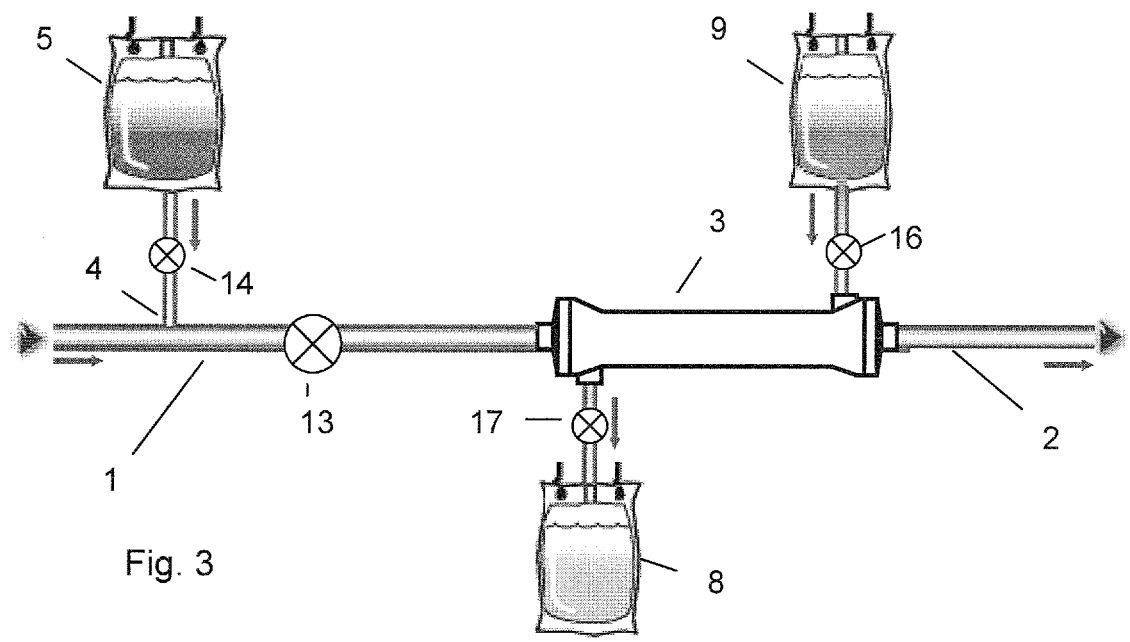

In FIG. 3 is shown a second system for citrate anticoagulation in an extracorporeal blood circuit. This system includes an arterial blood line 1 configured to be connected to a vascular access for withdrawing blood from a patient and a venous blood line 2 configured to be connected to the vascular access for returning blood to the patient. This system also comprises a filter 3 with a dialysate side and a blood side, which blood side is in fluid communication with the arterial and venous blood lines, and which dialysate side is in fluid communication with a dialysis fluid source 9 comprising 1.5-8 mM citrate and ≥10 mM bicarbonate and an effluent bag 8 for the spent dialysis fluid and the plasma water (ultrafiltrate) withdrawn from the blood passing the filter 3. The system further comprises a pre-filter infusion line 4 connected to the arterial blood line 1 upstream the filter 3 for infusing an anticoagulation fluid 5 comprising 15-40 mM citrate into the blood in the arterial blood line.

Figure 4:
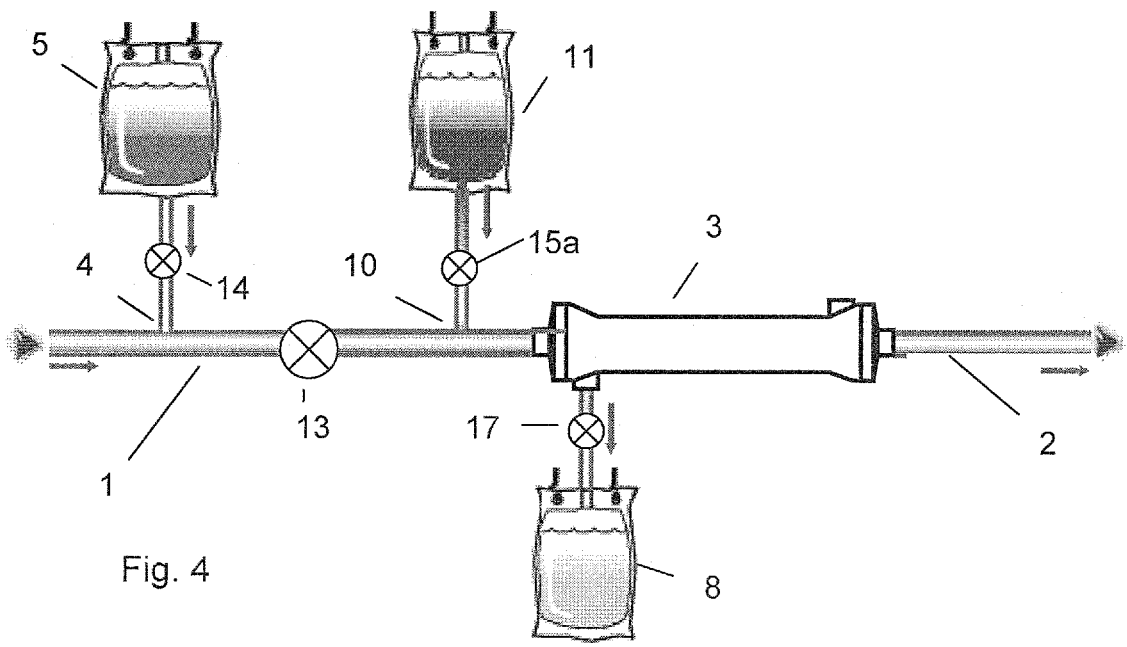

In FIG. 4 is shown a third embodiment of the system for citrate anticoagulation in an extracorporeal blood circuit according to the present invention. This system includes an arterial blood line 1 configured to be connected to a vascular access for withdrawing blood from a patient and a venous blood line 2 configured to be connected to the vascular access for returning blood to the patient. This system further comprises a filter 3 with a dialysate side and a blood side, which blood side is configured in fluid communication with the arterial and venous blood lines. A first pre-filter infusion line 4 is connected to the arterial blood line 1 upstream the filter 3 for infusing an anticoagulation fluid 5 comprising 15-40 mM citrate into blood in the arterial blood line 1. A second pre-filter infusion line 10 is connected to the arterial blood line 1 upstream the filter 3 for infusing an infusion fluid 11 1.5-8 mM citrate and ≥10 mM bicarbonate into blood in the arterial blood line 1. Also here an effluent bag 8 is provided in fluid communication with the dialysate side of the filter 3, for receiving the plasma water (ultrafiltrate) withdrawn from the blood passing the filter 3.

Figure 5:
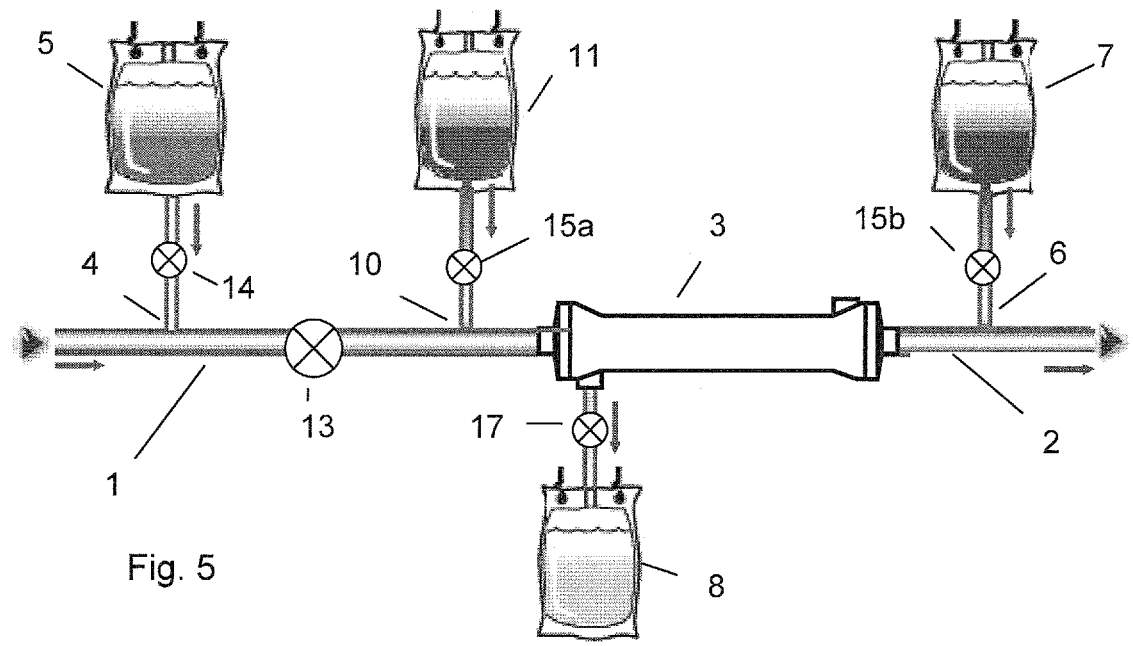

In FIG. 5 is another embodiment of the third system in FIG. 4 shown, which further comprises a post-filter infusion line 6 connected to the venous blood line 2 downstream the filter 3 for infusing an infusion fluid 7 comprising 1.5-8 mM citrate and ≥10 mM bicarbonate into blood in the venous blood line 2.

Figure 6:
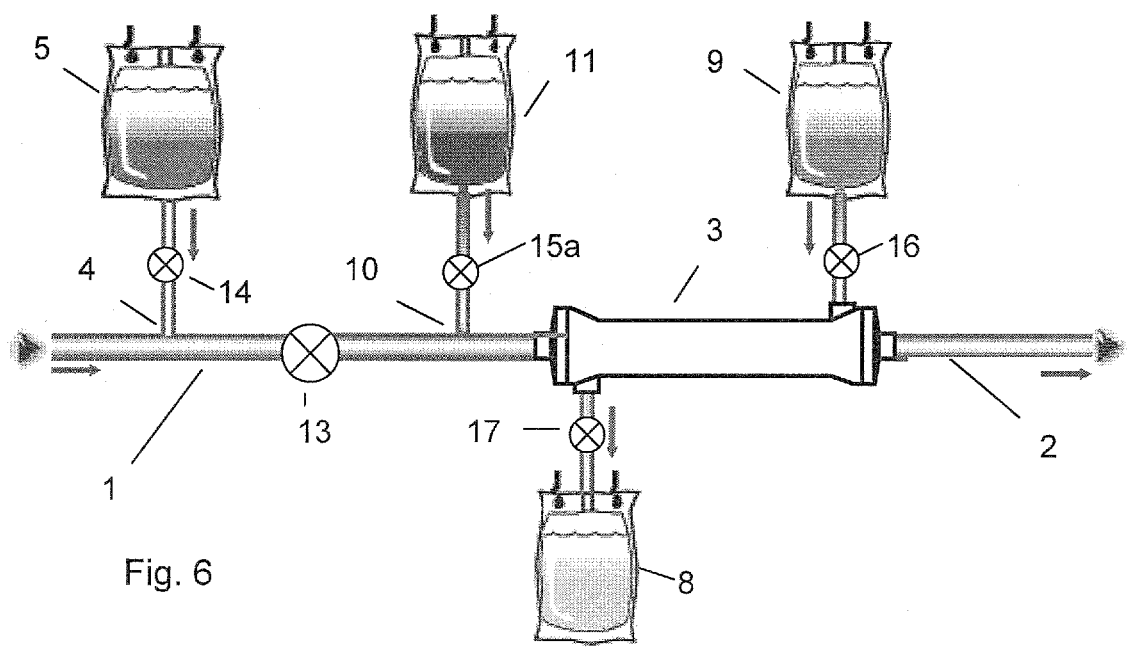

In FIG. 6 is yet another embodiment of the third system in FIG. 4 shown, wherein the dialysate side of the filter 3 is in fluid communication with a dialysis fluid source 9 comprising 1.5-8 mM citrate and ≥10 mM bicarbonate.

Figure 7:
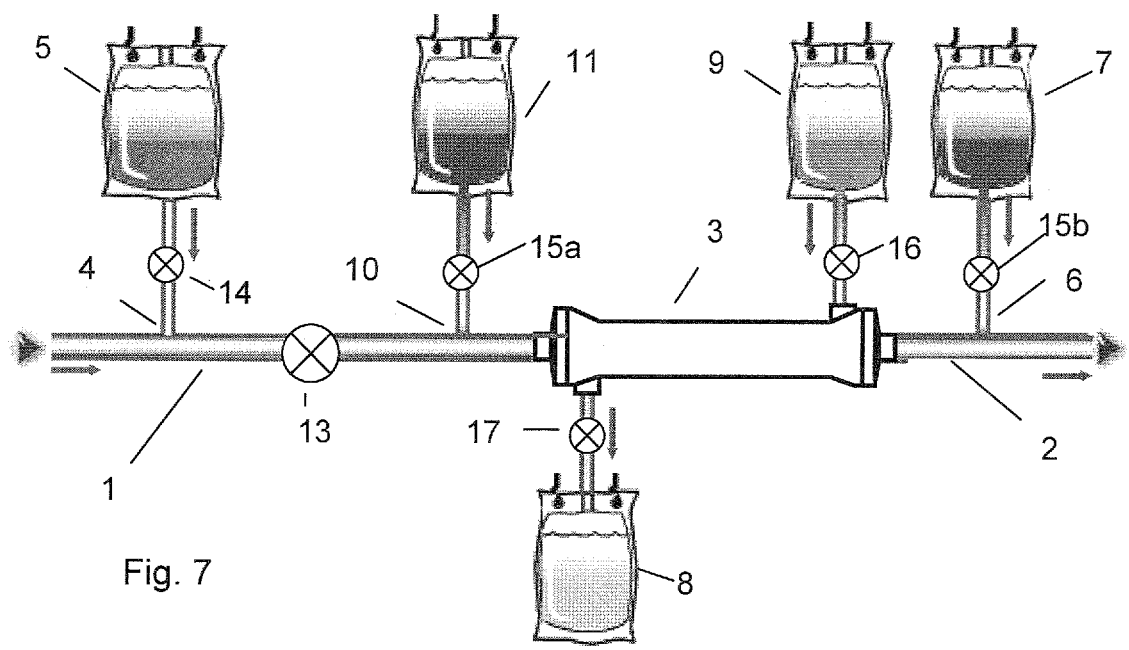

In FIG. 7 is another embodiment of the system in FIG. 6 shown. This system further comprises a post-filter infusion line 6 connected to the venous blood line 2 downstream the filter 3 for infusing an infusion fluid 7 comprising 1.5-8 mM citrate and ≥10 mM bicarbonate into the blood in the venous blood line 2.

Figure 8:
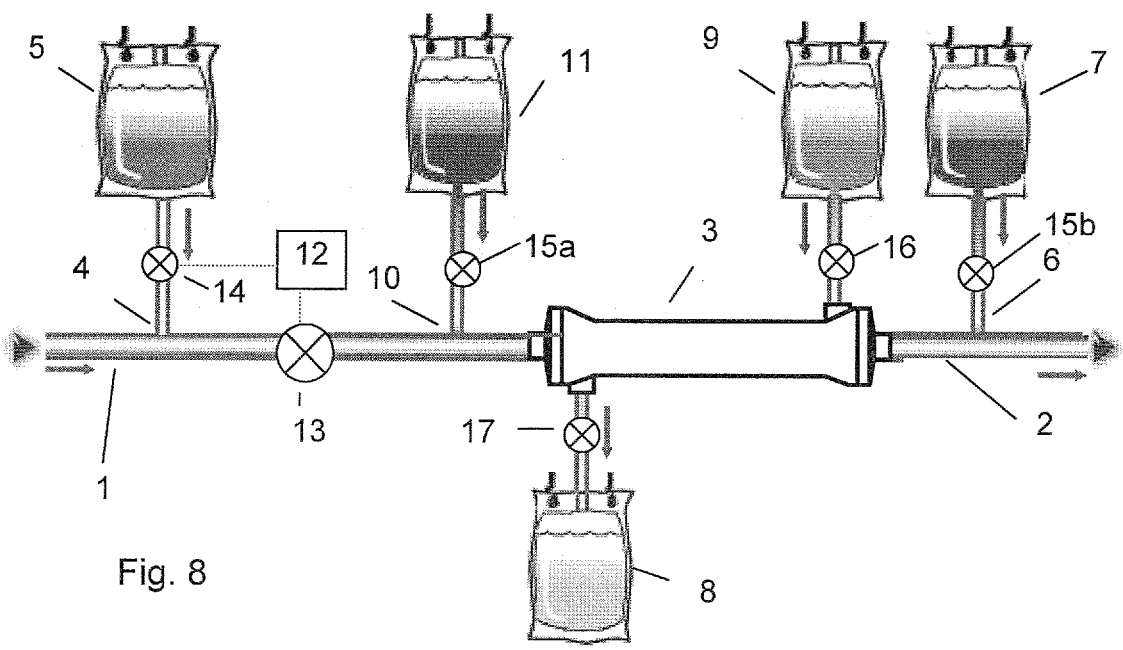

In FIG. 8 is another embodiment of the systems above shown, which further comprises a control unit 12 adapted to control the anticoagulation fluid flow rate in relation to the blood flow rate. Such a control unit may be provided in all the systems shown in the different embodiments of FIG. 1-FIG. 7. By having such a control unit 12, the system is monitoring and securing that the amount of citrate within the blood is enough to maintain anticoagulation within the extracorporeal blood circuit.

If 1-5 mM total calcium is present in at least one fluid from the group consisting of a dialysis fluid, an infusion fluid, and an anticoagulation fluid, the systems according to the present invention do not need to comprise any post-filter infusion line connected to the venous blood line 2 downstream the filter 3 for infusion of a fluid comprising >6 mM total calcium.

In the systems according to the invention, pumps are configured to pump blood (pump 13) through the extracorporeal blood circuit, anticoagulation fluid (pump 14) into the extracorporeal blood circuit, infusion fluid (pumps 15a and 15b) into the extracorporeal blood circuit, dialysis fluid (pump 16) into the dialysate side of the filter 3, and plasma liquid (ultrafiltrate) and optional spent dialysis fluid (pump 17) out from the dialysate side of the filter 3 and into the effluent bag 8.

EXAMPLES

By way of example, and not limitation, the following examples identify a variety of multipart fluid systems and systems for citrate anticoagulation pursuant to embodiments of the present invention.

Example 1

TABLE 1

| Component | Anticoagulation fluid | Infusion fluid for pre-infusion | Dialysis fluid |
|---|---|---|---|
| Citrate, (mM) | 30 | 4 | 4 |
| Bicarbonate, (mM) | 0 | 18 | 18 |
| Calcium, (mM) | 2.2 | 2.0 | 2.0 |
| Magnesium, (mM) | 0.5 | 0.5 | 0.5 |
| Potassium, (mM) | 3 | 3 | 3 |
| Glucose, (mM) | 0 | 0 | 5.5 |
| Sodium, (mM) | 140 | 140 | 140 |
| Phosphate, (mM) | 0.8 | 0.8 | 0.8 |

The multipart fluid system of table 1 can be used in a system for regional citrate anticoagulation according to FIG. 6.

Example 2

TABLE 2

| Component | Anticoagulation fluid | Infusion fluid for pre-infusion | Dialysis fluid |
|---|---|---|---|
| Citrate, (mM) | 30 | 5 | 5 |
| Bicarbonate, (mM) | 0 | 15 | 15 |
| Calcium, (mM) | 2.2 | 1.5 | 1.5 |
| Magnesium, (mM) | 0.5 | 0.5 | 0.5 |
| Potassium, (mM) | 3 | 3 | 3 |

TABLE 2-continued

| Component | Anticoagulation fluid | Infusion fluid for pre-infusion | Dialysis fluid |
|---|---|---|---|
| Glucose, (mM) | 5.5 | 5.5 | 5.5 |
| Sodium, (mM) | 140 | 140 | 140 |
| Phosphate, (mM) | 0.8 | 0.8 | 0.8 |

The multipart fluid system of table 2 can be used in a system for regional citrate anticoagulation according to FIG. 6.

Example 3

TABLE 3

| Component | Anticoagulation fluid | Dialysis fluid |
|---|---|---|
| Citrate, (mM) | 30 | 5 |
| Bicarbonate, (mM) | 0 | 15 |
| Calcium, (mM) | 2.2 | 1.5 |
| Magnesium, (mM) | 0.5 | 0.5 |
| Potassium, (mM) | 3 | 3 |
| Glucose, (mM) | 0 | 5.5 |
| Sodium, (mM) | 140 | 140 |
| Phosphate, (mM) | 0.8 | 0.8 |

The multipart fluid system of table 3 can be used in a system for regional citrate anticoagulation according to FIG. 3.

Example 4

TABLE 4

| Component | Anticoagulation fluid | Infusion fluid for post-infusion | Dialysis fluid |
|---|---|---|---|
| Citrate, (mM) | 35 | 3 | 3 |
| Bicarbonate, (mM) | 0 | 20 | 20 |
| Calcium, (mM) | 2.3 | 2.4 | 2.4 |
| Magnesium, (mM) | 0.75 | 0.75 | 0.75 |
| Potassium, (mM) | 2 | 2 | 2 |
| Glucose, (mM) | 0 | 0 | 5.5 |
| Sodium, (mM) | 140 | 140 | 140 |
| Phosphate, (mM) | 1.0 | 0 | 1.0 |

The multipart fluid system of table 4 can be used in a system for regional citrate anticoagulation according to FIG. 2.

Example 5

TABLE 5

| Component | Anticoagulation fluid | Infusion fluid for post-infusion | Dialysis fluid |
|---|---|---|---|
| Citrate, (mM) | 18 | 4 | 4 |
| Bicarbonate, (mM) | 0 | 20 | 20 |
| Calcium, (mM) | 2.3 | 2.4 | 2.4 |
| Magnesium, (mM) | 0.75 | 0.75 | 0.75 |
| Potassium, (mM) | 2 | 2 | 2 |
| Glucose, (mM) | 0 | 0 | 5.5 |
| Sodium, (mM) | 140 | 140 | 140 |
| Phosphate, (mM) | 1.0 | 0 | 1.0 |

Example 6

TABLE 6

| Component | Anticoagulation fluid | Infusion fluid for post-infusion | Dialysis fluid |
|---|---|---|---|
| Citrate, (mM) | 25 | 5 | 5 |
| Bicarbonate, (mM) | 0 | 17 | 17 |
| Calcium, (mM) | 2.3 | 2.4 | 2.4 |
| Magnesium, (mM) | 0.75 | 0.75 | 0.75 |
| Potassium, (mM) | 2 | 2 | 2 |
| Glucose, (mM) | 0 | 0 | 5.5 |
| Sodium, (mM) | 140 | 140 | 140 |
| Phosphate, (mM) | 1.0 | 0 | 1.0 |

Example 7

TABLE 7

| Component | Anticoagulation fluid | Infusion fluid for post-infusion | Dialysis fluid |
|---|---|---|---|
| Citrate, (mM) | 30 | 4 | 4 |
| Bicarbonate, (mM) | 0 | 16 | 16 |
| Calcium, (mM) | 2.3 | 2.4 | 2.4 |
| Magnesium, (mM) | 0.75 | 0.75 | 0.75 |
| Potassium, (mM) | 2 | 2 | 2 |
| Glucose, (mM) | 0 | 0 | 0 |
| Sodium, (mM) | 140 | 140 | 140 |
| Phosphate, (mM) | 1.0 | 0 | 1.0 |

Example 8

TABLE 8

| Component | Anticoagulation fluid | Infusion fluid for post-infusion | Dialysis fluid |
|---|---|---|---|
| Citrate, (mM) | 40 | 5 | 5 |
| Bicarbonate, (mM) | 0 | 12 | 12 |
| Calcium, (mM) | 2.3 | 2.4 | 2.4 |
| Magnesium, (mM) | 0.75 | 0.75 | 0.75 |
| Potassium, (mM) | 2 | 2 | 2 |
| Glucose, (mM) | 5.5 | 0 | 5.5 |
| Sodium, (mM) | 140 | 140 | 140 |
| Phosphate, (mM) | 1.0 | 0 | 1.0 |

The multipart fluid systems of tables 5-8 can be used in a system for regional citrate anticoagulation according to FIG. 2.

An aspect of the invention is a multipart fluid system for dialysis therapy, said multipart fluid system comprising an anticoagulation fluid and at least one treatment fluid from the group consisting of dialysis fluid and infusion fluids, wherein said anticoagulation fluid comprises 15-40 mM citrate; and said at least one treatment fluid comprises 1.5-8 mM citrate and ≥10 mM bicarbonate.

A second aspect of the invention is a multipart fluid system according to the aspect above, wherein said anticoagulation fluid comprises 18-40 mM citrate, preferably 20-30 mM citrate.

A third aspect of the invention is a multipart fluid system according to any of the aspects above, wherein said at least one treatment fluid comprises 10-30 mM bicarbonate, preferably 10-20 mM bicarbonate.

A fourth aspect of the invention is a multipart fluid system according to anyone of aspects herein, wherein said at least one treatment fluid comprises 1-5 mM total calcium.

A fifth aspect of the invention is a multipart fluid system according to anyone of the preceding aspects, wherein said at least one treatment fluid comprises 2.0-7.0 mM citrate and 1.5-2.4 mM total calcium.

A sixth aspect of the invention is a multipart fluid system according to anyone of the preceding aspects above, wherein said at least one treatment fluid comprises 3.5-5.5 mM citrate and 1.5-2.4 mM total calcium.

A seventh aspect of the invention is a multipart fluid system according to anyone of the preceding aspects, wherein said at least one treatment fluid further comprises 0-1.5 mM magnesium, 0-5.0 mM potassium, 0-11 mM glucose, 130-150 mM sodium.

An eighth aspect of the invention is a multipart fluid system according to anyone of the preceding aspects, wherein said at least one treatment fluid further comprises 0.1-2.0 mM phosphate, preferably 0.4-1.5 mM phosphate, more preferably 0.6-1.2 mM phosphate.

A ninth aspect of the invention is a multipart fluid system according to anyone of the preceding aspects, wherein said anticoagulation fluid comprises 1.5-4 mM total calcium, preferably 1.5-3 mM total calcium, more preferably 1.5-2.4 mM total calcium.

An tenth aspect of the invention is a multipart fluid system according to anyone of the preceding aspects, wherein said anticoagulation fluid further comprises 0-1.5 mM magnesium, 0-5.0 mM potassium, 0-11 mM glucose, 130-150 mM sodium.

An eleventh aspect of the invention is a multipart fluid system according to anyone of the preceding aspects, wherein said anticoagulation fluid further comprises 0.1-2.0 mM phosphate, preferably 0.4-1.5 mM phosphate, and most preferably 0.6-1.2 mM phosphate.

Another aspect of the invention is a multipart fluid system for dialysis therapy, said multipart fluid system comprising an anticoagulation fluid and at least one treatment fluid from the group consisting of dialysis fluid and infusion fluids, wherein said anticoagulation fluid comprises 10-40 mM citrate; and said at least one treatment fluid comprises 1.5-8 mM citrate and ≥10 mM bicarbonate.

Also, another aspect of the invention is a system encompassing the multipart fluid system as defined by any of the aspects described above.

An fourteenth aspect of the invention is a system for citrate anticoagulation in an extracorporeal blood circuit comprising an arterial blood line configured to be connected to a vascular access for withdrawing blood from a patient and a venous blood line configured to be connected to the vascular access for returning blood to the patient, the system comprising: a filter with a dialysate side and a blood side; which blood side is in fluid communication with the arterial and venous blood lines; and which blood side is in fluid communication with an anticoagulation fluid source comprising 15-40 mM citrate; a treatment fluid source comprising 1.5-8 mM citrate and ≥10 mM bicarbonate, and said treatment fluid source being in fluid communication with at least one of the blood side or dialysate side of the filter.

A fifteenth aspect of the invention is a system for citrate anticoagulation in an extracorporeal blood circuit according the aspects described above, which further comprises a post-filter infusion line connected to the venous blood line downstream the filter and connected to a treatment fluid source comprising, 1.5-8 mM citrate and ≥10 mM bicarbonate to be infused into the blood stream in the venous blood line.

A sixteenth aspect of the invention is a system for citrate anticoagulation in an extracorporeal blood circuit according to the fourteenth aspect, which further comprises a second pre-filter infusion line connected to the arterial blood line upstream the filter and connected to a treatment fluid source comprising 1.5-8 mM citrate and ≥10 mM bicarbonate to be infused into the blood stream in the arterial blood line.

A seventeenth aspect of the invention is a system for citrate anticoagulation in an extracorporeal blood circuit according to the sixteenth aspect, which further comprises a post-filter infusion line connected to the venous blood line downstream the filter and connected to an infusion fluid source comprising 1.5-8 mM citrate and ≥10 mM bicarbonate to be infused into the blood stream in the venous blood line.

An eighteenth aspect of the invention is a system for citrate anticoagulation in an extracorporeal blood circuit according to the fourteenth aspect above, where the treatment fluid source is in fluid communication with the dialysate side of the filter.

A nineteenth aspect of the invention is a system for citrate anticoagulation in an extracorporeal blood circuit according to any of the fourteenth to seventeenth aspects, wherein the dialysate side of the filter is in fluid communication with a dialysis fluid source comprising 1.5-8 mM citrate and ≥10 mM bicarbonate.

A twentieth aspect of the invention is a system for citrate anticoagulation in an extracorporeal blood circuit according to anyone of to any of the fourteenth to nineteenth aspects, wherein said anticoagulation fluid comprises 18-40 mM citrate, preferably 20-30 mM citrate.

A twentyfirst aspect of the invention is a system for citrate anticoagulation in an extracorporeal blood circuit according to anyone of to any of the fourteenth to twentieth aspects, wherein said system further comprises a control unit adapted to control the anticoagulation fluid flow rate in relation to the blood flow rate.

According to the present invention any combination of the aspects related to the multipart system as well as the system is included.

Calculations and Optimizations

Citrate is metabolised in the body, and theoretically each citrate ion is converted into three bicarbonate ions. Citrate will therefore contribute to the acid base balance, and it is important to consider the contribution from citrate when citrate is included in the treatment fluids. In citrate anticoagulation rather high concentrations of citrate is needed in the anticoagulation fluid in order to get sufficient anticoagulative effect. This is even more pronounced with the multipart fluid system for dialysis therapy and the system for citrate anticoagulation in an extracorporeal blood circuit according to the present invention, especially in the embodiments wherein citrate also is present in the treatment fluids, like the dialysis fluid and/or the replacement fluids. We will now illustrate how the bicarbonate levels should be adjusted when citrate is used in order to get the best acid base balance in the patient.

In these calculations and optimizations it is assumed that each citrate ion is converted into three bicarbonate ions in the body, and the term "bicarbonate equivalents" is used for the sum of the bicarbonate concentration and three times the citrate concentration. Since most intensive care patients are catabolic, more acid than normal will be produced, and the treatment fluids need to be alkalotic. The treatment efficiency is usually rather low, thus the contents of bicarbonate equivalents in the treatment fluids need to be rather high. In non-citrate therapies the bicarbonate concentration is often about 35 mM. Depending on the bicarbonate level in the untreated blood, the bicarbonate level in the blood that is returned to the patient is then around or slightly above 30 mM. It seems to be reasonable to attempt to achieve the same level of bicarbonate equivalents also when citrate is used, but since the conversion of citrate to bicarbonate may take some time the level of bicarbonate equivalents in the returning blood actually need to be slightly higher (see below). The goal is to find the best level of bicarbonate equivalents in the dialysis and replacement fluids for a given level of citrate in the anticoagulant.

Below, all flow rates are denoted with Q and the concentrations with C, both with an index to indicate which flow is referred to. Index pre denotes the flow of anticoagulant (pre), index d is dialysate, r is replacement (only postdilution considered), e is effluent, b is whole blood, p is plasma, o is plasma out (returned to patient). WL denotes the weight loss rate, x is the dose of citrate for anticoagulation in mM citrate per liter blood, and α is the fraction of plasma in whole blood. Thus the variables are as follows:

Qb—flow rate of whole blood in to the system (L/h)
Qp—flow rate of plasma in to the system (L/h)
Qpre—flow rate of anticoagulation fluid (L/h)
Qd—flow rate of dialysis fluid (L/h)
Qr—flow rate of replacement fluid (postdilution) (L/h)
Qe—flow rate of effluent fluid (used treatment fluid) (L/h)
WL—weight loss rate (L/h)
Cb—bicarbonate equivalents in untreated whole blood (mM)
Cp—bicarbonate equivalents in untreated plasma (mM)
Co—bicarbonate equivalents in treated plasma (mM)
Cpre—bicarbonate equivalents in anticoagulation fluid (mM)
Cd—bicarbonate equivalents in dialysis fluid (mM)
Cr—bicarbonate equivalents in replacement fluid (mM)
x—dose of citrate (mM per liter of blood)
α—fraction of plasma in whole blood There are some immediate relations $$Qp = \alpha \cdot Qb \tag{1}$$

$$Qpre \cdot Cpre = x \cdot Qb \tag{2}$$

The flow rate of effluent must match the flow rate of treatment fluids together with the weight loss rate so that $$Qe = Qpre + Qd + Qr + WL \tag{3}$$

The treatment efficiency is low in intensive care, which means that the concentration in the effluent flow can be assumed to be equilibrated with the untreated plasma entering the dialyzer. This implies $$Ce \cdot (Qpre + Qp) = Cpre \cdot Qpre + Cp \cdot Qp \tag{4}$$

Everything going into the dialyzer must equal everything that comes out. Thus $$Cpre \cdot Qpre + Cp \cdot Qp + Cd \cdot Qd + Cr \cdot Qr = Ce \cdot Qe + Co \cdot (Qp - WL) \tag{5}$$

It will be assumed that the dialysis and replacement fluids have the same composition, so that Cd=Cr. By rearranging (5) we then get $$Cd \cdot (Qd + Qr) = Ce \cdot Qe - Cpre \cdot Qpre - Cp \cdot Qp + Co \cdot (Qp - WL) \tag{6}$$

The first 3 terms on the right hand side of (6) can be simplified using first (4), then (3), and finally (4) again. We have $$Ce \cdot Qe - Cpre \cdot Qpre - Cp \cdot Qp = Ce \cdot (Qe - Qpre - Qp) \quad (7)$$
$$= Ce \cdot (Qd + Qr + WL - Qp) =$$
$$= \frac{Cpre \cdot Qpre + Cp \cdot Qp}{Qpre + Qp} \cdot$$
$$= (Qd + Qr + WL - Qp)$$

Qb is eliminated by inserting (1) into (2), Qpre is eliminated by inserting (2) into (7), and then insert (7) into (6) to get $$Cd \cdot (Qd + Qr) = \frac{x \cdot Qp/\alpha + Cp \cdot Qp}{x \cdot Qp/\alpha/Cpre + Qp} \cdot (Qd + Qr + WL - Qp) + Co \cdot \quad (8)$$
$$(Qp - WL) =$$
$$= \frac{Cpre}{x/\alpha + Cpre} \cdot (x/\alpha + Cp) \cdot$$
$$(Qd + Qr + WL - Qp) + Co \cdot (Qp - WL)$$

With the help of (8) we can study how the dialysis fluid concentration should be changed depending on the anticoagulation concentration if we want to keep the same concentration in the returning blood (which is the last term). For this purpose we can assume that the weight loss rate WL is zero, and that α, x, Qp, Cp and Co are fixed. Since Qp is always (in intensive care) greater than Qd+Qr we see that Cd should be decreased when Cpre is increased. This change is nonlinear with Cpre, and when Cpre is much larger than x/α there will be no further decrease in Cd. With x in the range 3-5 mM and α=0.7 there will thus not be much further decrease in Cd when Cpre is above about 50 mM.

It is also advantageous if the blood outlet concentration of bicarbonate equivalents does not vary too much when the flow rate of dialysis or replacement fluid is changed, since it is then possible to adjust the treatment dose by changing these flow rates without disturbing the acid base balance. We can see from (8) that the influence from Qd and Qr will disappear totally if $$Cd = \frac{Cpre}{x/\alpha + Cpre} \cdot (x/\alpha + Cp) \quad (9)$$

This value for Cd might lead to a too low value for Co, and it could also be valuable to have a nonzero, but small influence on acid base from the flow rates. So a slightly higher Cd than given by (9) is preferable.

In order to verify the results from these equations a number of simulations have been performed according to common principles for simulations. With the fluid concentrations and flow rates specified, the program calculates the resulting concentrations in the blood returned to the patient. The goal for the simulations was to find a suitable level of bicarbonate equivalents in the dialysis and replacement fluids for each specified level in the anticoagulation fluid. This was done by adjusting the level in the treatment fluids until the plasma level in the returned blood was as desired (chosen as 32.5 mM).

The simulation program is developed in-house by Gambro. It computes equilibrium concentrations of species present in plasma and fluids used for dialysis by use of equilibrium constants (SCD base 2001[1]). The species (electrolytes, albumin and formed complexes) taken into account are shown in Table A.

TABLE A

Normal plasma concentration of electrolytes and albumin together with the complexes taken into account formed with $Ca^{2+}$ and $Mg^{2+}$

| Specie | Normal plasma total conc (mM) (Kratz 1998[2]) | Complex formation with $Ca^{2+}$ and $Mg^{2+}$ |
|---|---|---|
| $Ca^{2+}$ | 2.1-2.6 (1.1-1.3 ionized) | |
| $Mg^{2+}$ | 0.7-1.0 | |
| $Na^+$ | 135-145 | |
| $Cl^-$ | 100-108 | |
| $HCO_3^-$, bicarbonate, bic | 22-26 | $CaHCO_3^+$, $MgHCO_3^+$ |
| $C_6H_5O_7^{3-}$, citrate, cit | 0.1-0.3 (infants, Ames1950[3]) | Ca-cit$^-$, Ca-cit$_2^{4-}$, Mg-cit$^-$. Mg-cit$_2^{4-}$ |
| Albumin, alb | 0.5-0.6 | Alb-Ca$_n$, alb-Mg$_n$, n = 1-10 |

The transport of each species is governed by its mobility and the flow rates of plasma and dialysis fluid. Values for the mobility of different species are found in literature. The transport of ions is also affected by the demand for electroneutrality, which is expressed as the development of a membrane potential. In order to handle the effects of complex formations and albumin binding, the dialyzer is split up into a number of segments and the transport calculations are performed in an iterative manner. The transport across the dialyzer membrane in one segment leads to a new equilibrium for the complex formation and albumin binding, which forms the input to the next segment for the next iteration. About 30 iterations are needed to find the equilibrium concentrations along the entire dialyzer.

The requirements of the treatments are:
1. An adequate dialysis treatment A sufficient anticoagulant effect, i.e. the ionized calcium through the blood side of the filter (dialyzer) must be 0.2-0.5 mM, preferably 0.3-0.4 (according to literature)
2. The total plasma concentration of calcium when returned to the patient has to be at normal level, i.e. about 2.2-2.4 mM. Other electrolyte concentration levels must also be satisfactory.

The simulations were performed with a blood flow rate of 100 ml/min, a hematocrit of 30%, an albumin level of 30 g/L and no patient weight loss. The plasma concentrations in the incoming blood were 25 mM of bicarbonate, 0.85 mM of magnesium, 2.2 mM of calcium and no citrate. The dialysis and replacement fluids contained 5 mM of citrate, 2.1 mM of calcium and 0.85 mM of magnesium. These levels reflect the content in the plasma in the dialyzer, which is fairly independent of the other variables and are chosen in order to keep the balance. The anticoagulation fluid contained 2.2 mM of calcium, 0.85 mM of magnesium and no bicarbonate. The citrate level in the anticoagulation fluid was varied from 12 to 400 mM, and its flow rate was adjusted so that the level of ionized calcium after the dialyzer was always 0.3 mM, which is considered to be an adequate level for anticoagulation. The bicarbonate level in the dialysis and replacement fluids was varied as needed to keep the bicarbonate equivalents in the returned blood unchanged at 32.5 mM. The dialysis and replacement fluid flow rates (equally large) were chosen in each simulation so that the clearance (treatment dose) was the same (=2700 L/h) in all cases. Since the amount of anticoagulation fluid, which is delivered as a predilution addition, contributes to the clearance, but also decreases it due to dilution, it was necessary have different flow rates of replacement fluid and dialysis fluid for each case.

FIG. 9 shows the bicarbonate level needed in the treatment fluids for varying citrate levels in the anticoagulation fluid. As expected from the theoretical formula (8) the bicarbonate level needed in the treatment fluids decreases with increasing citrate level in the anticoagulation fluid.

Figure 10:
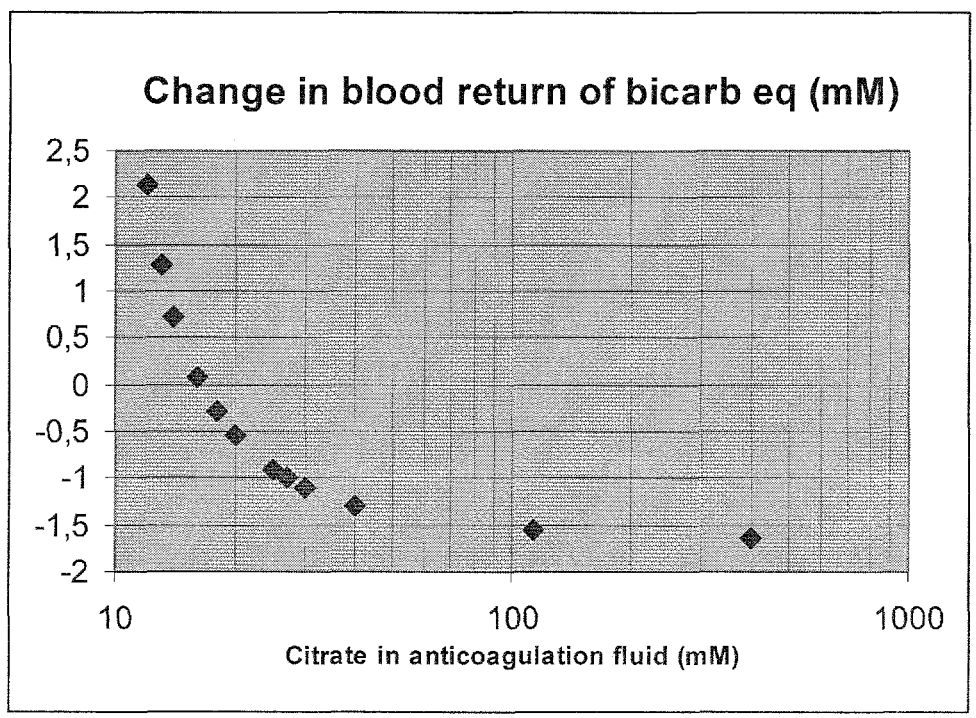
FIG. 10 illustrates the change of bicarbonate equivalents in the treated blood.

A second set of simulations were performed in order to evaluate the sensitivity of the level of bicarbonate equivalents in the returned blood to changes in treatment dose. The dose was in for all the cases increased to 3500 L/h by appropriate adjustments of the dialysis and replacement flow rates (still equal to each other), but all other parameters were kept unchanged. FIG. 10 shows the change in bicarbonate equivalents in the returning blood as a function of the citrate level in the anticoagulation fluid. It can be seen that the lowest sensitivity is for an anticoagulation fluid with about 16 mM of citrate. The change in bicarbonate equivalents is less than 1.3 mM for citrate levels between 13 and 40 mM, and is below 1 mM for citrate levels between 14 and 27 mM. The exact values for these ranges will depend slightly on all the other parameters, and these simulations should therefore only be used as a rough guideline.

Pilot Study

A non-randomized pilot study including five patients has been performed. All patients included in the study showed acute renal failure and CRRT was started at the general intensive care unit at Skane University Hospital in Lund, Sweden by using the dialysis fluid Phoxilium (Gambro) and the infusion fluid Hemosol B0 (Gambro) according to the standards at the unit and the extracorporeal circuit was anticoagulated with heparin. The treatment mode was Continuous Venous Venous Hemodiafiltration (CVVHDF). After onset of CRRT, the patients were monitored the first treatment day to assure stability in vital physiological parameters and a well functioning central dialysis catheter. Then the treatment scheme was changed to the multipart fluid system for citrate anticoagulation according to the present invention for a period of five hours. A new CRRT machine with a fresh filter was primed with the study fluids and at initiation of the study period this machine was connected to the patient.

During the study period the patients were subjected to intense monitoring, regular blood sampling and were supervised by a physician present bedside. After completed CRRT regime with multipart fluid system according to the present invention, the patient continued the CRRT treatment using the standard fluids.

In all patients the Gambro Prismaflex machine and a Hospal M100 AN 69 filter was used during the study period.

The compositions of the fluids for the study were as described below in table B. The system was set up according to FIG. 2.

TABLE B

Compositions of anticoagulation fluid, dialysis fluid and infusion fluid used in the study:

| Component: | Anticoagulation fluid (5) mM | Dialysis fluid (9) mM | Infusion fluid (7) mM |
|---|---|---|---|
| Citrate$_{tot}$ | 40 | 4.4 | 4.4 |
| Ca$_{tot}$ | 2.4 | 2.2 | 2.2 |
| Mg$_{tot}$ | 0.9 | 0.9 | 0.9 |
| K$^+$ | 4 | 4 | 4 |
| Cl$^-$ | 31.2 | 123.3 | 123.3 |

TABLE B-continued

Compositions of anticoagulation fluid, dialysis fluid and infusion fluid used in the study:

| Component: | Anticoagulation fluid (5) mM | Dialysis fluid (9) mM | Infusion fluid (7) mM |
|---|---|---|---|
| Na$^+$ | 140 | 140 | 140 |
| bicarbonate$_{tot}$ | — | 15 | 15 |

Blood flow ($Q_B$) was set to 100 ml/min. Anticoagulation fluid flow ($Q_{PBP}$) was set to 730 ml/h, and dialysis fluid flow as well as infusion fluid flow ($Q_d$ and $Q_{inf}$) was set to 1000 ml/h.

Results

Acid-base variables and serum electrolytes at the beginning and at the end of the treatment using the compositions of Table B are shown in Table C. Serum ionized calcium ($Ca^{2+}$) and phosphate concentrations decrease significantly at the start of the citrate treatment, but remained thereafter stable during the study period. Serum concentrations of sodium (Na$^+$), potassium (K$^+$), magnesium (Mg$^{2+}$) and chloride (Cl$^-$) remained also stable. No alkalosis or acidosis occurred during the citrate treatment, as the acid-base balance with the pH, carbon dioxide partial pressure (pCO$_2$) and bicarbonate (HCO$_3^-$) concentrations, as well as the calculated acid-base variables, all remained stable (see Table C). Also included are ions which are routinely not measured, thus unidentified strong anions (UA-) are included. Examples of such ions are lactate, keto-acids and sulphate. UA$^-$ may be calculated by (Na$^+$+K$^+$+Ca$^{2+}$+Mg$^{2+}$)−(($Cl^-$)$_{corrected}$+SID)).

TABLE C

Acid-base variables and the concentrations of serum electrolytes

| | Normal values$^a$ | Start | End | p=$^b$ |
|---|---|---|---|---|
| Na$^+$, mM | 137-145 | 137 ± 3 | 136 ± 3 | 0.667 |
| K$^+$, mM | 3.5-4.4 | 4.3 ± 0.5 | 4.6 ± 0.5 | 0.358 |
| Ca$^{2+}$, mM | 1.16-1.35 | 1.2 ± 0.05 | 1.1 ± 0.04 | 0.008 |
| Mg$^{2+}$, mM | 0.70-0.95 | 0.9 ± 0.1 | 0.9 ± 0.1 | 0.421 |
| Cl$^-$, mM | 98-110 | 107 ± 3 | 106 ± 2 | 0.379 |
| phosphate, mM | 0.7-1.5 | 0.9 ± 0.03 | 0.7 ± 0.1 | 0.008 |
| Alb, g/l | 36-48 | 27 ± 5 | 27 ± 3 | 0.874 |
| pH | 7.35-7.45 | 7.42 ± 0.04 | 7.43 ± 0.05 | 0.709 |
| pCO$_2$, kPa | 4.6-6.0 | 4.9 ± 0.4 | 4.8 ± 0.4 | 0.646 |
| HCO$_3^-$, mM | 22-27 | 24.1 ± 2.6 | 24.6 ± 1.8 | 0.773 |
| AG$_{measured}$, mM | 16 ± 2 | 10 ± 4 | 10 ± 2 | 0.813 |
| AG$_{corrected}$,$^c$ mM | 16 ± 2 | 14 ± 3 | 15 ± 1 | 0.794 |
| BE, mM | −3.0-+3.0 | −0.3 ± 3 | −0.2 ± 2 | 0.980 |
| SID, mM | 39 ± 1 | 35 ± 4 | 36 ± 2 | 0.607 |
| Cl$^-_{corrected}$,$^c$ mM | 98-110 | 111 ± 4 | 110 ± 2 | 0.665 |
| UA$^-$, mM | 8 ± 2 | 3 ± 3 | 3 ± 1 | 0.702 |
| UA$^-_{corrected}$,$^c$ mM | 8 ± 2 | −1 ± 5 | −1 ± 3 | 0.991 |
| A$^-_{tot}$, mM | 15 | 9 ± 1 | 9 ± 1 | 0.841 |

$^a$Normal values from healthy controls (Fend, 2000$^4$) and reference values at Clinical Chemistry Laboratory, Skane University Hospital, Lund, Sweden.
$^b$Differences between values at the beginning and at the end of the treatment
$^c$Corrected for water excess/deficit A high lactate level (>5 mM) in patients with liver failure or septic patients, may act as a useful marker of greater risk for citrate accumulation. The lactate levels were low in our patients before the treatment with the fluids according to the study, and remained stable during the treatment. Serum citrate levels were increased at the beginning of the treatment, but remained constant during the study and reached a peak value of 0.61 mM after two hours of treatment. Post-filter ionized calcium values remained statistically stable around 0.37 mM (Table D). The patients were initially low in total calcium concentration, and remained below normal total calcium value (2.1-2.6 mM) throughout the study period (Table D). An initial drop in ionized calcium was observed in the total to ionized calcium ratio, but the ratio remained stable below 2.25, with no clinical signs of citrate accumulation. No problem with the filter or with the CRRT circuit arose during the treatment period, and all values on the CRRT machine remained inside the normal intervals.

TABLE D

Calcium homeostasis

| | Time (h) | | | |
|---|---|---|---|---|
| | 0 | 2 | 5 | $p^b =$ |
| $Ca^{2+}$ extracorporeal$^a$, mM | $0.37 \pm 0.04$ | $0.37 \pm 0.03$ | $0.38 \pm 0.04$ | 0.409 |
| $Ca_{tot}$, mM | $2.15 \pm 0.15$ | $2.22 \pm 0.11$ | $2.28 \pm 0.09$ | 0.171 |
| $Ca^{2+}$, mM | $1.24 \pm 0.05$ | $1.12 \pm 0.04$ | $1.14 \pm 0.04$ | 0.008 |
| $Ca_{tot}/Ca^{2+}$ ratio | $1.74 \pm 0.13$ | $1.97 \pm 0.11$ | $1.96 \pm 0.06$ | 0.017 |

$^a$Measured post-filter
$^b$Differences between values at the beginning and at the end of the treatment Since the first report in the early 90ies, citrate anticoagulation in CRRT patients has gained interest. Citrate has been associated with longer circuit life, less bleeding, and possibly better patient and kidney survival compared to heparin. Despite these findings, citrate anticoagulation is often perceived as complex and associated with high risk for metabolic derangements. These concerns are based on cumbersome protocols and the more labour intensive monitoring. We have now designed new fluids for citrate anticoagulation where calcium and citrate are balanced with electrolytes at physiological concentrations in order to maintain the extracorporeal anticoagulation, keep patient calcium homeostasis, minimize metabolic complications and especially restore and maintain acid-base balance within the patient. The citrate and calcium-containing dialysis fluids kept the calcium concentrations below the recommended 0.40 mM in the extracorporeal circuit and no clotting occurred during this study.

Metabolic derangements during citrate anticoagulation include alkalosis and acidosis, hypernatremia and hyponatremia, and hypocalcemia. The incidence of these complications depends on citrate concentration and the design of the protocol. Acid-base data in critically ill patients are often interpreted on the basis of either plasma bicarbonate concentration ($HCO_3^-$) and "anion gap" (AG), or on the "base excess/deficit" (BE). However, hypoalbuminemia and hyper/hypophosphatemia regularly found in critically ill patients are not taken into account in these parameters. Therefore we used the Stewart concept[5] of acid-base to calculate the metabolic effect of citrate and analysed the strong ion difference during conditions of abnormal albumin concentrations and water excess/deficit found in critically ill patients. The citrate and calcium-containing dialysis fluids and infusion fluids did not have metabolic effects on the patients. As no substitution of phosphate was done during this study, serum phosphate levels were significantly affected. Systemic ionized calcium levels stabilized after initial decline and ranged from 1.12 to 1.25 mM after five hours of citrate treatment. There were no instances of clinically significant hypocalcemia, and no adjustments of the infusion rate were needed.

Accumulation of citrate can occur if its metabolism is insufficient. As citrate accumulation decreases the ionized calcium, and increases the total calcium concentration, the total to ionized calcium ratio is a useful test to detect citrate accumulation. The total to ionized calcium ration stabilised at 1.97 mM after two hours of treatment, well below 2.25 mM that would trigger consideration of probable citrate accumulation. Citrate accumulation can also increase the anion gap, although this variable is not sensitive in critically ill patients. In this study we used a fixed dose of citrate (5 mM per liter blood) in relation to blood flow to target optimal anticoagulation. This citrate dose is higher than the previously recommended target at 3 mM, albeit no significant systemic effect was noticed. Serum citrate reached a stable concentration of 0.4-0.7 mM with infusion fluid rates ranging from 1 to 2 l/h, suggesting that citrate was not accumulated in our patients. These results are comparable with previously published serum citrate concentration of 1.04±0.46 mM in 23 patients treated with 2,2% ACD CVVHDF (ACD, Anticoagulant Citrate Dextrose[6]). As a readily available substrate for the cellular citric acid cycle, low concentrations of systemic citrate may also have anti-inflammatory benefits. Intermediates from metabolized citrate were shown to protect proximal tubules against injury and promote recovery from sustained mitochondrial energetic deficit. Recently, an in vitro study showed that citrate at a concentration of 0.8 mM reduces endothelial inflammation and dysfunction during hypoglycemic state.

In this pilot study, the novel concept for citrate anticoagulation was investigated, with the aim of eliminating the need for the final replacement of lost calcium and particularly with the aim to safeguard a proper acid-base balance within the patient. Not properly done, calcium infusion represents an increased risk for the patient, but also an increased complexity and cost of the treatment. Previous attempts to eliminate calcium replacement have failed, either because of filter clotting due to ineffective anticoagulation, or to the need of calcium infusions due to inadequate calcium substitution. The basic principle for the novel method is to keep the concentration of total calcium unchanged in the whole extracorporeal circuit by an appropriate amount of calcium in all treatment fluids. Furthermore, concentration of citrate in the anticoagulation fluids is sufficient to complex excess calcium, and even though the total calcium level is within physiological limits, the level of ionized calcium in the extracorporeal circuit is kept low. To succeed with this context, citrate was included in the dialysis and infusion fluids. Thus, the use of the multipart fluid system according to the present invention significantly contributed to simplification of citrate anticoagulation by omitting the continuous infusion of calcium.

Furthermore, these dialysis fluids and/or infusion fluids in particular attained patients' acid-base balance and no circuit problems occurred during the treatment. With the balanced anticoagulation fluids together with the dialysis fluids and/or infusion fluids of the present invention the possibility to vary the flow rates of the different fluids within the multipart fluid system in a large interval without causing any acid-base imbalance within the patient is also provided.

While the invention has been described in connection with what is presently considered to be the most practical embodiments, it is to be understood that the invention is not to be limited to the disclosed embodiments, but on the contrary, is intended to cover various modifications and equivalents included within the spirit and the scope of the appended claims.

REFERENCES

[1] SCDbase, Stability Constants Database IUPAC, Academic Software, 2001
[2] Kratz A et al.; New Engl J Med 339:1063-1067, 1998

[3] Ames R et al.; Pediatrics 6:361-370, 1950
[4] Fencl V., Jabor A., Kazda A., Figge J., (2000), Diganosis of metabolic acid-base disturbances in critically ill patients. Am. J. Respir. Crit. Care Med 162: 2246-2251.
[5] Stewart P A, (1983) Modern quantitative acid-base chemistry. Can J Physiol Pharmacol 61: 1444-1461
[6] Ronco C., Critical Care Nephrology, (2009), p1296

The invention claimed is:

1. A multipart fluid system for dialysis therapy, the multipart fluid system comprising:
   an anticoagulation fluid; and
   at least one treatment fluid from the group consisting of dialysis fluid and infusion fluids, wherein the anticoagulation fluid comprises 15-40 mM citrate, the at least one treatment fluid comprises 1.5-8 mM citrate and >10 mM bicarbonate, and wherein a level of the bicarbonate in the at least one treatment fluid is selected from a set of bicarbonate levels that satisfy a relationship in which the level of the bicarbonate is decreased with increased citrate levels in the anticoagulation fluid.

2. The multipart fluid system according to claim 1, wherein said anticoagulation fluid comprises 18-40 mM citrate.

3. The multipart fluid system according to claim 1, wherein said at least one treatment fluid comprises 10-30 mM bicarbonate.

4. The multipart fluid system according to claim 1, wherein said at least one treatment fluid comprises 1-5 mM total calcium.

5. The multipart fluid system according to claim 1, wherein said at least one treatment fluid comprises 2.0-7.0 mM citrate and 1.5-2.4 mM total calcium.

6. The multipart fluid system according to claim 1, wherein said at least one treatment fluid comprises 3.5-5.5 mM citrate and 1.5-2.4 mM total calcium.

7. The multipart fluid system according to claim 1, wherein said at least one treatment fluid further comprises 0-1.5 mM magnesium, 0-5.0 mM potassium, 0-11 mM glucose, 130-150 mM sodium.

8. The multipart fluid system according to claim 1, wherein said at least one treatment fluid further comprises 0.1-2.0 mM phosphate.

9. The multipart fluid system according to claim 1, wherein said anticoagulation fluid comprises 1.5-4 mM total calcium.

10. The multipart fluid system according to claim 1, wherein said anticoagulation fluid further comprises 0-1.5 mM magnesium, 0-5.0 mM potassium, 0-11 mM glucose, 130-150 mM sodium.

11. The multipart fluid system according to claim 1, wherein said anticoagulation fluid further comprises 0.1-2.0 mM phosphate.

12. The multipart fluid system according to claim 1, wherein the level of the bicarbonate is decreased from 20 mM to 12 mM with increased citrate levels from 18 mM to 40 mM in the anticoagulation fluid.

\* \* \* \* \*